(12) United States Patent
Achyuta et al.

(10) Patent No.: US 9,555,235 B2
(45) Date of Patent: Jan. 31, 2017

(54) MULTI-LAYERED MICRO-CHANNEL ELECTRODE ARRAY WITH REGENERATIVE SELECTIVITY

(71) Applicant: The Charles Stark Draper Laboratory, Inc., Cambridge, MA (US)

(72) Inventors: Anilkumar H. Achyuta, Cambridge, MA (US); Bryan L. McLaughlin, Cambridge, MA (US); James Hsiao, Watertown, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 139 days.

(21) Appl. No.: 14/605,148

(22) Filed: Jan. 26, 2015

(65) Prior Publication Data
US 2015/0217109 A1 Aug. 6, 2015

Related U.S. Application Data

(60) Provisional application No. 61/934,037, filed on Jan. 31, 2014.

(51) Int. Cl.
*A61N 1/05* (2006.01)
*A61F 2/02* (2006.01)
(Continued)

(52) U.S. Cl.
CPC ........... *A61N 1/0551* (2013.01); *A61B 5/4893* (2013.01); *A61F 2/025* (2013.01); *A61N 1/36103* (2013.01);
(Continued)

(58) Field of Classification Search
CPC .................................................. A61B 5/4893
See application file for complete search history.

(56) References Cited

U.S. PATENT DOCUMENTS 7,615,063 B2 * 11/2009 Doi .................... A61B 17/1128
606/152

2007/0260170 A1 11/2007 Levin et al. .................... 604/20
(Continued)

FOREIGN PATENT DOCUMENTS

CN 101 912 666 A 12/2010 ............... A61N 1/05
WO WO 2006/009722 1/2006 ............. G06F 15/16
(Continued)

OTHER PUBLICATIONS

International Searching Authority, International Search Report—International Application No. PCT/US2015/012856, dated Apr. 28, 2015, together with the Written Opinion of the International Searching Authority, 11 pages.
(Continued)

*Primary Examiner* — Carl H Layno
*Assistant Examiner* — Jennifer Ghand
(74) *Attorney, Agent, or Firm* — Sunstein Kann Murphy & Timbers LLP

(57) ABSTRACT

A scaffold defines a plurality of channels, into which axons of a severed nerve may regenerate, such as after limb amputation. Each channel includes a corresponding electrode. Regenerating axons may make electrical contact with the electrodes. Each channel is at least partially filled with a growth factor selected to selectively stimulate axon regeneration. Adjacent channels may include different growth factors, so as to attract different types of axons, for example efferent axons and afferent axons, to each of the adjacent channels. The growth factors may be distributed in the channels so as to present a gradient across a geometry of each channel. This gradient provides enhanced differentiated geometric guidance to the axons, thereby yielding better specificity, in terms of which axons regenerate into which channels. Topography, such as geometric patterns in walls, ceilings and floors of the channels, may also be used to selectively encourage axon regeneration into the channels.

16 Claims, 18 Drawing Sheets

(51) Int. Cl.
  *A61B 5/00* (2006.01)
  *A61B 5/04* (2006.01)
  *A61N 1/36* (2006.01)

(52) U.S. Cl.
  CPC .......... *A61B 5/04001* (2013.01); *A61B 5/6877* (2013.01); *A61F 2250/0067* (2013.01); *A61N 1/36003* (2013.01)

(56) References Cited

U.S. PATENT DOCUMENTS

| | | | |
|---|---|---|---|
| 2008/0300691 A1 | 12/2008 | Romero-Ortega et al. | 623/23.72 |
| 2010/0152699 A1 | 6/2010 | Ferrari et al. | 604/500 |
| 2011/0021943 A1 | 1/2011 | Lacour et al. | 600/546 |
| 2011/0250585 A1 | 10/2011 | Ingber et al. | 435/5 |
| 2013/0253606 A1 | 9/2013 | Youn et al. | 607/48 |

FOREIGN PATENT DOCUMENTS

| | | | |
|---|---|---|---|
| WO | WO 2008/122044 | 10/2008 | A61N 1/18 |
| WO | WO 2012/139124 | 10/2012 | A61B 5/05 |

OTHER PUBLICATIONS

Lehew, et al., "State-of-the-Art Microwire Array Design for Chronic Neural Recordings in Behaving Animals", Chapter 1, Methods for Neural Ensemble Recordings, 2nd Edition, 29 pages, 2008.

Lotfi, et al., "Modality-specific axonal regeneration: toward selective regenerative neural interfaces", Frontiers in Neuroengineering, vol. 4, Article 11, 11 pages, Oct. 2011.

Subbaraman, "Controlling Prosthetic Limbs with Electrode Arrays", MIT Technology Review, Biomedicine News, 4 pages, Apr. 2011.

Wieringa, et al., "Neural Growth Into a Microchannel Network: Towards a Regenerative Neural Interface", Proceedings of the 4$^{th}$ International IEEE EMBS Conference on Neural Engineering, 5 pages, 2009.

\* cited by examiner

MULTI-LAYERED MICRO-CHANNEL ELECTRODE ARRAY WITH REGENERATIVE SELECTIVITY

CROSS REFERENCE TO RELATED APPLICATIONS

This application claims the benefit of U.S. Provisional Patent Application No. 61/934,037, filed Jan. 31, 2014, titled "Multi-Layered Micro-Channel Electrode Array with Regenerative Selectivity," the entire contents of which are hereby incorporated by reference herein, for all purposes.

TECHNICAL FIELD

The present invention relates to nerve electrode arrays and, more particularly, to multi-channel nerve electrode arrays that contain growth factors to selectively promote nerve regeneration into the channels.

BACKGROUND ART

Limb amputations can significantly negatively impact amputees' lives. Fortunately, prosthetic devices can partially compensate for loss of limb structure (bone, skin, etc.) and actuation (muscle). An ideal, albeit not yet developed, prosthetic device would include a separate motor for each lost muscle or degree of limb freedom, and each such motor would be driven by a discrete signal from the amputee's nervous system. Similarly, the ideal prosthetic device would include a sensor (touch, temperature, etc.) corresponding to each sense signal the amputated limb would otherwise have sent to the amputee's nervous system.

In a nervous system, efferent axons, otherwise known as motor or effector neurons, carry nerve impulses from a central nervous system to effectors, such as muscles and glands. On the other hand, afferent axons, otherwise known as sensory nerves or receptor neurons, carry nerve impulses from receptors or sense organs towards the central nervous system. Neural interfaces are, therefore, important for coupling efferent and afferent nerves to motors and sensors, respectively, in prosthetic devices.

Interfacing with efferent and afferent axons is difficult, at least in part due to their small sizes. In general, as illustrated in FIG. 1, a peripheral nerve 100 includes blood vessels 102 and several fascicles 104, each fascicle containing a bundle of axons 106. A typical human fascicle is about 500μ in diameter.

In some prior art nerve interfaces, three electrodes are disposed longitudinally along a nerve or a fascicle. Two of the electrodes are used to establish an electrical reference voltage, and the third electrode provides an electrical measurement signal. However, the electrical measurement provides an integrated signal, i.e., a sum of signals from a plurality of axons in the nerve or fascicle. A fascicle contains a combination of efferent and afferent axons, and all the efferent axons typically do not control a single muscle. Thus, the integrated measurement signal is of limited value for selectively driving a motor of a prosthetic device.

Higher density neural interfaces, i.e., interfaces that provide an electrical signal from a small numbers of axons, ideally from one axon, would facilitate finer motor control in prosthetic devices than is achievable in the prior art. Similarly, higher density neural interfaces would facilitate more granular sensory feedback from prosthetic devices to central nervous systems.

SUMMARY OF EMBODIMENTS

Embodiments of the present invention provide scaffolds, into which severed nerves may regenerate, such as after limb amputations. The scaffold includes a plurality of channels, i.e., three-dimensional volumes bounded on most, but not all, sides by walls, a floor and a ceiling. Each channel has one or more corresponding electrodes. Axons may regenerate into respective channels and there make electrical contact with the electrodes. The channels are decorated with bioactive matrixes and/or mechanical surface properties that selectively promote growth of nerve fibers.

For example, each channel may be at least partially filled with a growth factor selected to stimulate axon regeneration. Adjacent channels may include different growth factors, so as to attract different types of axons, for example efferent and afferent axons, to each of the adjacent channels. The growth factors may be distributed in the channels so as to present a gradient across a geometry, such as width or height, of each channel, as detected by regenerating axons. These gradients provide enhanced differentiated geometric guidance to the axons, thereby yielding better specificity, in terms of which axons regenerate into which channels. Optionally or alternatively, topography, such as geometric patterns in walls, floors and ceilings of the channels, such as raised bumps of various shapes, may be used to selectively encourage axon regeneration into the channels.

An embodiment of the present invention provides an electrode array. The electrode array includes a bio-compatible dielectric scaffold. The bio-compatible dielectric scaffold defines a plurality of openings and a plurality of channels in the bio-compatible dielectric scaffold. Each channel occupies a three-dimensional volume extending into the scaffold from a respective opening of the plurality of openings. Each channel contains an electrode attached to the scaffold and electrically exposed to the three-dimensional volume of the channel. Each channel contains a bio-compatible gel disposed in the channel. The electrode array also includes a first growth factor disposed in the gel disposed in a first at least one of the plurality of channels. The first growth factor is selected to preferentially promote growth of a first type of nerve fiber over a second type of nerve fiber. The electrode array also includes a second growth factor disposed in the gel disposed in a second at least one of the plurality of channels. The second at least one of the plurality of channels is different than the first at least one of the plurality of channels. The second growth factor is selected to preferentially promote growth of the second type of nerve fiber over the first type of nerve fiber.

The first type of nerve fiber may include afferent nerve fiber, and the second type of nerve fiber may include efferent nerve fiber.

The first type of nerve fiber may include a first type of efferent nerve fiber, and the second type of nerve fiber may include a second type of efferent nerve fiber. The second type of nerve fiber may be different than the first type of efferent nerve fiber.

The first type of nerve fiber may include skin efferent nerve fiber, and the second type of nerve fiber may include muscle efferent nerve fiber.

The first growth factor may include at least one of: a close homolog of L1 (CHL1), L1-CAM and neurocan. The second growth factor may include at least one of netrin-1, semaphorin III and neuropilin-1.

The first growth factor may be disposed in the gel disposed in the first at least one of the plurality of channels so as to present a first gradient of effectiveness of the first growth factor across the opening of the first at least one of the plurality of channels. The second growth factor may be disposed in the gel disposed in the second at least one of the plurality of channels so as to present a second gradient of effectiveness of the second growth factor across the opening of the second at least one of the plurality of channels. The first gradient may increase along a direction away from the opening of the second at least one of the plurality of channels. The second gradient may increase along a direction away from the opening of the first at least one of the plurality of channels.

The plurality of channels may be arranged in a two-dimensional array. The electrode array may also include a third growth factor disposed in the gel disposed in a third at least one of the plurality of channels so as to present a third gradient of effectiveness of the third growth factor across the opening of the third at least one of the plurality of channels. A fourth growth factor may be disposed in the gel disposed in a fourth at least one of the plurality of channels so as to present a fourth gradient of effectiveness of the fourth growth factor across the opening of the fourth at least one of the plurality of channels. The respective openings of the first, second, third and fourth at least one of the plurality of channels may be arranged in a 2×2 array. The third gradient may increase along a direction away from the opening of the first at least one of the plurality of channels. The fourth gradient may increase along a direction away from the opening of the second at least one of the plurality of channels.

The first, second, third and fourth gradients may increase along respective directions radially away from a point surrounded by the respective openings of the first, second, third and fourth at least one of the plurality of channels.

The plurality of channels may be arranged in a two-dimensional array.

Each opening may have a major diameter no greater than about 200μ.

For each channel of the plurality of channels, the scaffold may define a back wall that defines an extent to which the three-dimensional volume of the channel extends into the scaffold.

For each channel of the plurality of channels, the growth factor disposed in the gel disposed in the channel may be conjugated to the gel.

Another embodiment of the present invention provides an electrode array that includes a bio-compatible dielectric scaffold. The bio-compatible dielectric scaffold defines a plurality of openings and a plurality of channels in the bio-compatible dielectric scaffold. Each channel occupies a three-dimensional volume extending into the scaffold from a respective opening of the plurality of openings. Each channel contains an electrode attached to the scaffold and electrically exposed to the three-dimensional volume of the channel. Each channel is defined at least in part by at least one wall of the scaffold. The at least one wall defines a three-dimensional surface pattern. The surface pattern of a first channel of the plurality of channels is different than the surface pattern of a second channel of the plurality of channels.

For each channel of the plurality of channels, the electrode array may include a bio-compatible gel disposed in the channel. A first growth factor may be disposed in the gel disposed in a first at least one of the plurality of channels. The first growth factor may be selected to preferentially promote growth of a first type of nerve fiber over a second type of nerve fiber. A second growth factor may be disposed in the gel disposed in a second at least one of the plurality of channels. The second at least one of the plurality of channels may be different than the first at least one of the plurality of channels. The second growth factor may be selected to preferentially promote growth of the second type of nerve fiber over the first type of nerve fiber.

The surface pattern of the first channel of the plurality of channels may include rectangular bumps, pyramidal bumps and/or round bumps.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

In accordance with embodiments of the present invention, methods and apparatus are disclosed for interfacing with nerve fibers, such as axons. These embodiments provide multi-channel scaffolds with better selectivity, in terms of guiding selected types of regenerating nerve fibers to specific channels of a scaffold, than the prior art. Electrodes in the channels may be used to record and/or stimulate the nerve fibers, thereby facilitating interfacing limb stumps or otherwise severed nerves with prosthetic devices.

Figure 1:
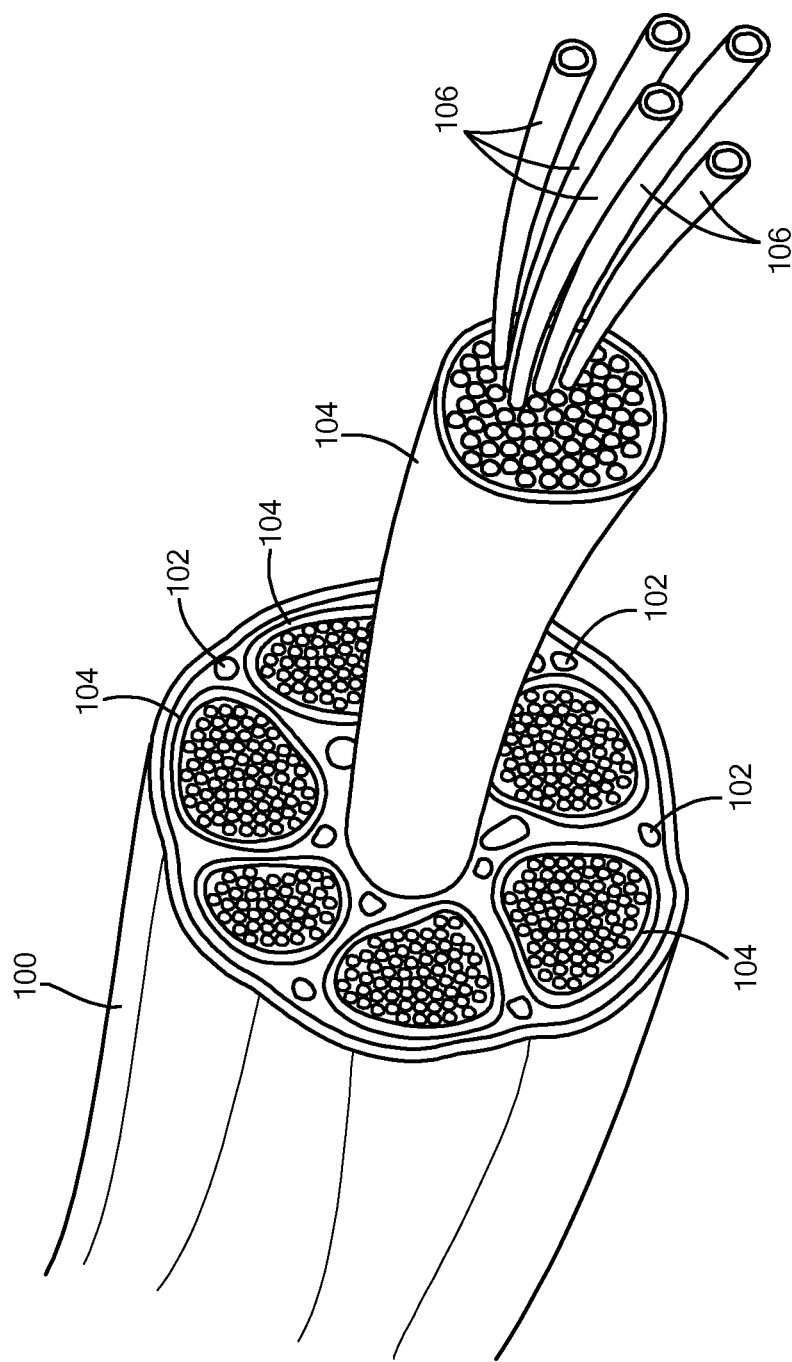
FIG. 1 is a perspective schematic illustration of a peripheral nerve, including fascicles and other items found in the nerve, as is well known in the art.
Figure 2:
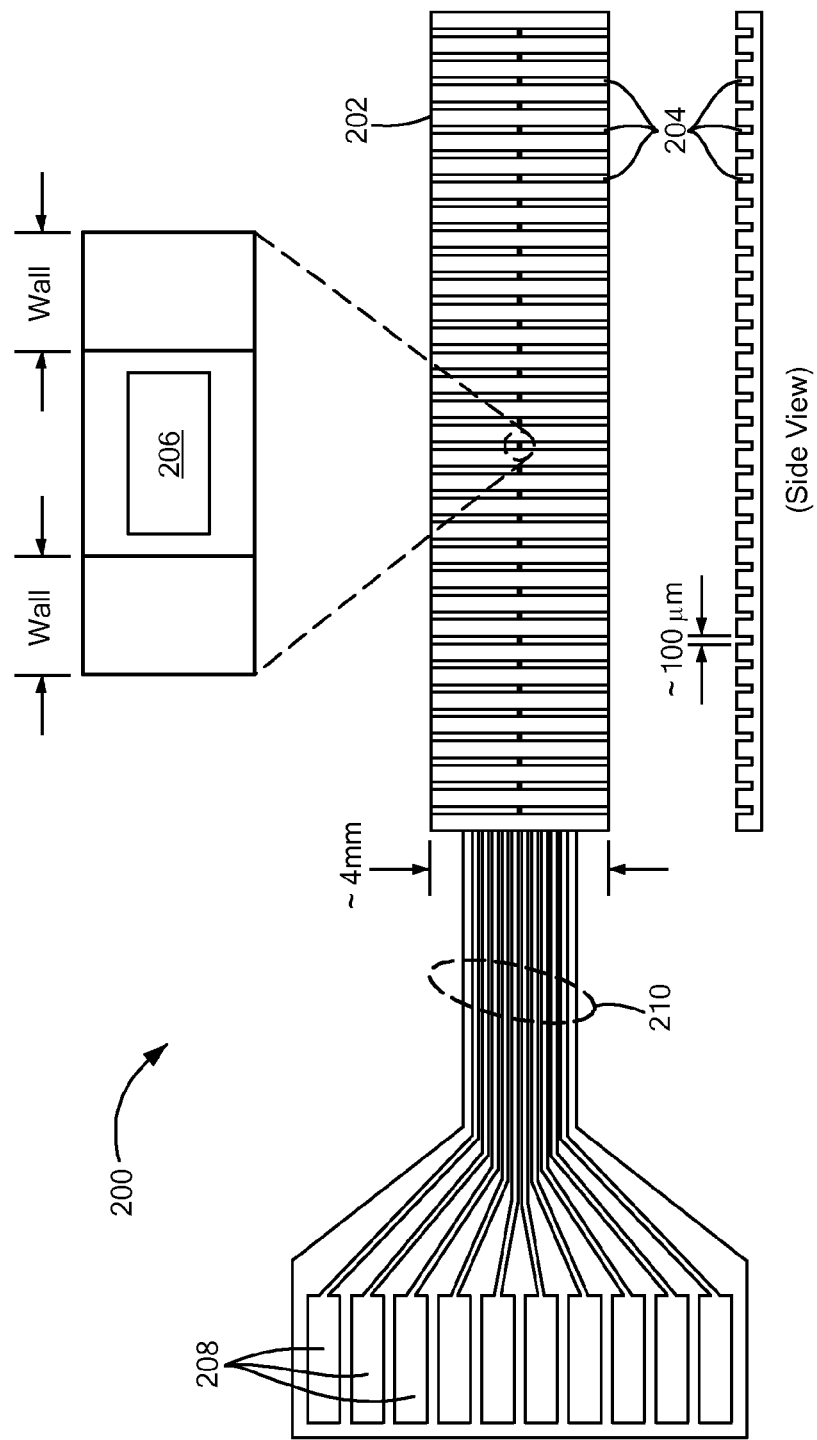
FIG. 2 is a plan view of a "jelly roll" nerve electrode array, according to the prior art.

Some prior art attempts to interface with nerves involve inserting an electrode array between two portions of a severed nerve. The nerve may have been severed as a result of an injury, or the nerve may be severed during surgery for the purpose of inserting the electrode array. FIG. 2 is a plan view of a prior art "jelly roll" nerve electrode array 200, before it is rolled up. The nerve electrode array 200 includes a flexible plate 202 defining a plurality of parallel groves 204, also shown in side view. Each of the groves 204 includes an exposed electrode, as exemplified by electrode 206 in the enlarged portion of the figure. Each electrode 206 is electrically connected to a respective contact pad 208, for connection to an external circuit. As shown schematically in FIG. 3, the flexible plate 202 is rolled around a mandrel 300 to form an approximate cylinder 400, schematically illustrated in FIG. 4. Returning to FIG. 3, adjacent layers of the spiral-wound flexible plate 202 cap the groves 204 of the layer below to form channels 302 extending longitudinally through the cylinder.

Figures 3, 4:
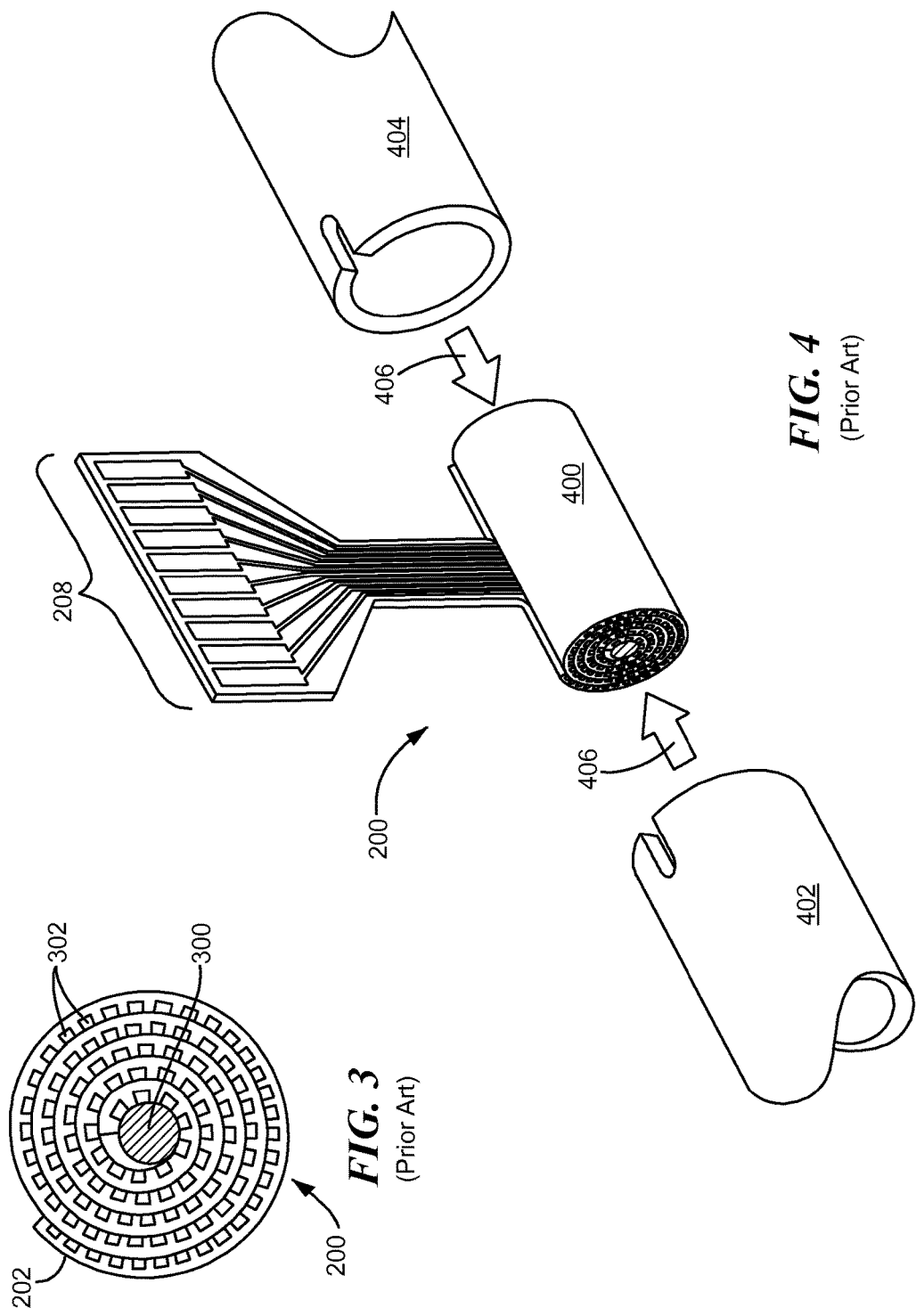
FIG. 3 is an end view of the nerve electrode array of FIG. 2, once the electrode array has been rolled upon a mandrel.
FIG. 4 illustrates nerve pieces being attached to the nerve electrode array of FIG. 3.
Figure 5:
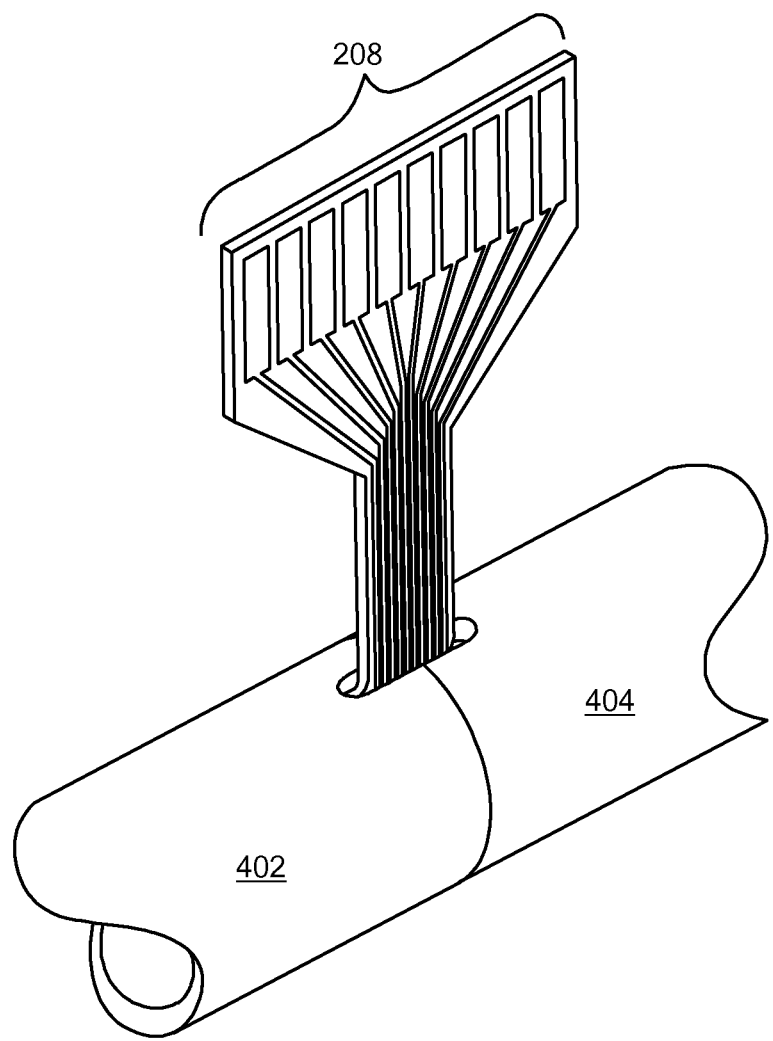
FIG. 5 illustrates the nerve pieces having been attached to the nerve electrode array.

In use, a nerve is severed into two pieces 402 and 404, as shown schematically in FIG. 4. Each piece 402 and 404 of the nerve is butted to, or slightly overlaps, a respective end of the cylinder 400, as indicated by arrows 406, yielding a configuration schematically illustrated in FIG. 5. Theoretically, axons from both of the severed nerve pieces 402 and 404 regenerate through the channels 302 and rejoin within the cylinder 400. Thus, the cylinder provides a scaffold for the axons to regenerate. Once a regenerated axon reaches its corresponding electrode 206 (FIG. 2), theoretically electrical signals from the axon may be detected by a circuit coupled to the contact pads 208.

Problematically, the mandrel 300 (FIG. 3) blocks the central portion (in cross section) of the cylinder 400, thereby preventing axon regeneration through the core of the cylinder. The central portions (in cross section) of the nerve pieces 402 and 404 are typically the most important, in terms of nerve pulse transmission. Therefore, the prior art jelly-roll nerve electrode array 200 blocks, or at least inhibits, regeneration of the most important axons, and it includes no electrodes to interface with these important axons.

In addition, the number of electrodes, and therefore channels, that can be individually electrically connected to an external circuit is limited by density of electrical interconnects 210 (FIG. 2) between the electrodes 206 and the contact pads 208. In a state-of-the-art jelly-roll nerve electrode array, only about 20 electrical connections can be accommodated. To put this number in perspective, a human arm has 22 degrees of freedom. Therefore, at least 22 distinct electrical connections to electrodes and a similar number of distinct channels are needed to drive a fully animated prosthetic arm. If more than one electrode per channel and/or neural feedback to the central nervous system is desired, additional electrical connections are required. In many cases, dozens or hundreds of distinct electrical connections are desired.

Figure 8:
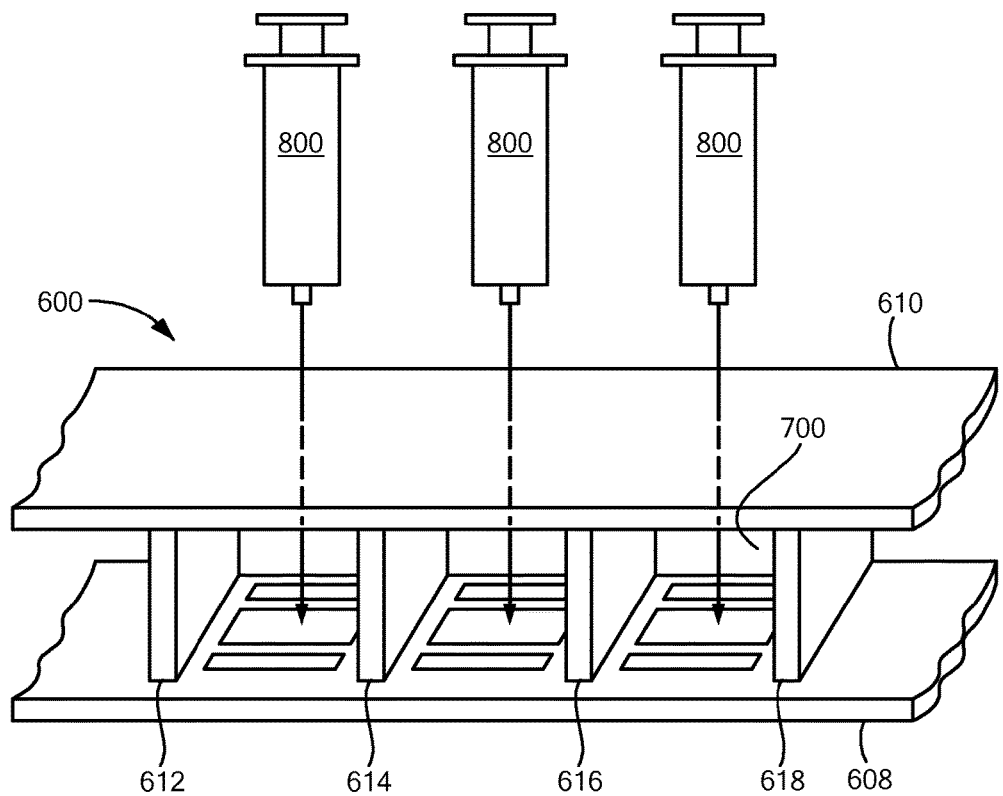
FIG. 8 schematically illustrates injecting growth factor into channels of the electrode array of FIG. 6, according to an embodiment of the present invention.

Placing more than one jelly-roll nerve electrode array in parallel to accommodate additional electrical connections creates additional problems, such as mismatches between geometry of the nerve (essentially round) and geometry of the faces of the electrode arrays (FIG. 8 for two arrays, etc.) Furthermore, if three or more electrode arrays are placed in parallel, gaps are formed among the cylinders 400 of the electrode arrays. These gaps provide no scaffolding or electrodes, yet axons might regenerate through them.

Furthermore, regeneration of the axons through the channels 302 is not specific. That is, any axon, or group of axons, may attempt to regenerate through a given channel 302. Thus, it is difficult or impossible to predict which type of axons, for example efferent or afferent, muscle or glad, etc., will regenerate through a given channel 302 and, therefore, it is difficult or impossible to predict whether electrical signals should be sensed from, or injected into, the channel's electrode 206, or which signals to expect to be associated with the channel's electrode.

If more than one efferent axon regenerates through a single channel 302, the electrical signals available at the corresponding contact pad 208 would be a combination of signals from more than one axon. Worse, if an afferent axon and an efferent axon both regenerate through a single channel 302, electrical stimulation introduced by a circuit through the channel's electrode 206 could cause undesirable side effects.

Embodiments of the present invention overcome these and other shortcomings of the prior art. An embodiment of the present invention provides a scaffold, into which a severed nerve may regenerate, such as after amputation of a limb. The scaffold includes a plurality of channels, each channel having one or more corresponding electrodes. Axons may regenerate into respective channels and there make electrical contact with the electrodes. Each channel is at least partially filled with a growth factor selected to stimulate axon regeneration. Adjacent channels may include different growth factors, so as to attract different types of axons, for example efferent and afferent axons, to each of the adjacent channels. The growth factors may be distributed in the channels so as to present a gradient across a geometry of each channel, as detected by regenerating axons. This gradient provides more differentiated geometric guidance to the axons, thereby yielding better specificity, in terms of which axons regenerate into which channels. Optionally or alternatively, topography, such as geometric patterns in walls, ceilings and floors of the channels, may be used to selectively encourage axon regeneration into the channels.

It should be noted that prior art jelly-roll nerve electrode arrays are intended to repair a break in a nerve, whereas most embodiments of the present invention are intended to be attached to only one end of a nerve, such as in a limb stump.

Figure 6:
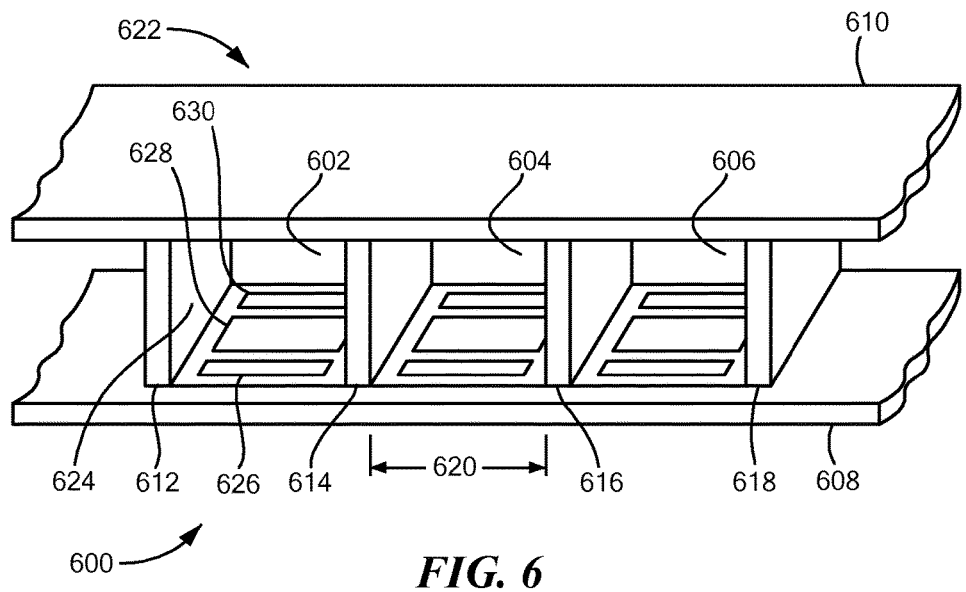
FIG. 6 is a perspective schematic view of a portion of an electrode array, according to an embodiment of the present invention.

FIG. 6 is a perspective illustration of a portion of an electrode array 600, according to an embodiment of the present invention. The portion of the electrode array 600 illustrated in FIG. 6 includes three channels 602, 604 and 606; however any number of channels may be included. The channels 602-606 are defined by a bottom substrate 608, a top substrate 610 and walls 612, 614, 616 and 618. Each channel is about 200μ wide, as indicated at 620, to accommodate an axon; however, other sizes of channels may be used, depending on expected sizes of axons. The bottom substrate 608, top substrate 610, walls 612-618 and back wall (described below) may be made of a bio-compatible material, such as polydimethylsiloxane (PDMS). (As used herein, the term "wall" includes ceiling, floor and back wall.)

The bottom substrate 608, the top substrate 610 and the walls 612-618 form a scaffold 622 into which axons of a severed nerve can regenerate. Each axon may regenerate into a channel defined by the scaffold 622. Each channel 602-606 occupies a three-dimensional volume extending into the scaffold 622 from an opening in the scaffold 622, an example of which is opening 624. Opening 624 to the channel 602 is referred to herein as a "front opening" and a "front end" of the channel 602. If the channel 602 has another opening at its other end, the other opening is referred to as a "back opening" and a "back end." Although channels with square openings are shown, the channel openings may be any shape, and not all openings need to be identically shaped or sized.

Each channel 602-606 includes at least one electrode electrically exposed to the three-dimensional volume of the channel. The electrode may be made of platinum or any other suitable material. In the embodiment shown in FIG. 6, each channel 602-606 includes three electrodes, exemplified by electrodes 626, 628 and 630 in channel 602. In some embodiments, two electrodes, such as electrodes 626 and 630, provide a reference voltage, and a third electrode, such as electrode 628, is used to sense (record) signals in an axon in the channel 602 or to inject signals into the axon to stimulate the axon. However, other numbers of electrodes per channel may be used. For example, the electrode 628 may be smaller, and a plurality of small electrodes (not shown) may be distributed parallel to electrode 628, between electrodes 626 and 630.

Figure 7:
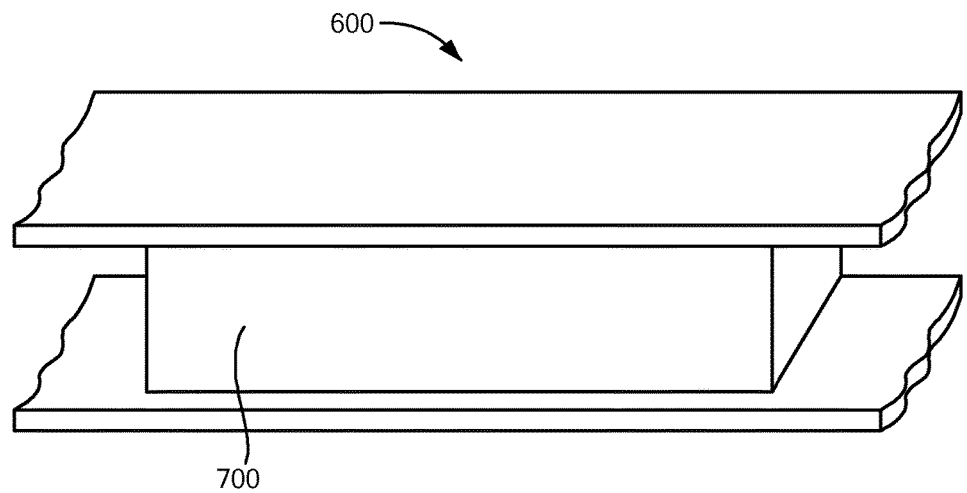
FIG. 7 is a rear perspective schematic view of the electrode array of FIG. 6.

FIG. 7 is a perspective schematic view of the electrode array 600 from the rear. A back wall 700 defines an end of the channels 602-606. Thus, each channel 602-606 is a "dead end." In other embodiments (not shown), the back wall 700 may be omitted, such as to permit axons from another portion of the nerve to regenerate into the back ends of the channels 602-606 and rejoin the axons regenerating into the front ends of the channels.

As noted, each channel 602-606 is at least partially filled with a growth factor selected to stimulate axon regeneration. The growth factor may be introduced into the channels 602-606 using any appropriate procedure, such as injecting the growth factor using hollow needles 800, as schematically illustrated in FIG. 8. If needles 800 are used, the material of the bottom substrate 608, top substrate 610, wall 612-618 or back 700, through which the needle is inserted, should be selected to sufficiently "heal" after the needle is withdrawn.

Figure 9:
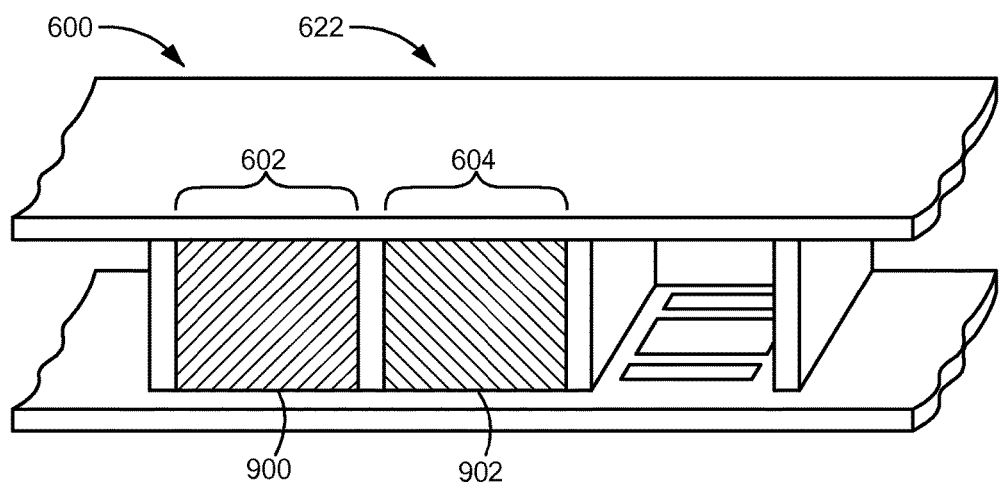
FIG. 9 schematically illustrates two channels of the electrode array of FIG. 6 filled with material that includes two different growth factors, according to an embodiment of the present invention.

FIG. 9 schematically illustrates two channels 602 and 604 filled with material that includes growth factors. One channel 602 is filled with a material 900 containing a first growth factor selected to at least preferentially promote growth of a first type of nerve fiber, such as efferent axons, and the other channel 604 is filled with a material 902 containing a second growth factor, different than the first growth factor, selected to at least preferentially promote growth of a second type of nerve fiber, such as afferent axons, different than the first type of nerve fiber. Any suitable growth factor or combination of growth factors may be used. For example, the first growth factor may include a close homolog of L1 (CHL1), L1-CAM or neurocan, and the second growth factor may include netrin-1, semaphorin III or neuropilin-1.

The growth factors may be selected to selectively promote growth of different types of afferent nerve fibers into the respective channels 602 and 604. For example, the first growth factor may be selected to promote growth of touch afferent nerve fiber into channel 602, and the second growth factor may be selected to promote growth into channel 604 of an afferent nerve fiber that carries signals from a stretch receptor, such as an intrafusal muscle fiber (a type of afferent neuron that lies parallel to an extrafusal muscle fiber and thus functions as a stretch receptor by detecting muscle length).

The growth factors may be selected to selectively promote growth of different types of efferent nerve fibers into the respective channels 602 and 604. For example, the first growth factor may be selected to promote growth of thumb muscle efferent nerve fiber into channel 602, and the second growth factor may be selected to promote growth of finger muscle efferent nerve fiber into channel 604.

To prevent the growth factors from leaking out of their respective channels 602 and 604, such as due to the force of gravity, each growth factor may be disposed in a gel, such as agarose gel. Agarose gel forms a matrix that holds the growth factor in place, yet the agarose gel generally does not interact with biomolecules, thereby making it suitable for use in vivo. The gel may also be used to hold the growth factor in a desired two-dimensional or three-dimensional location within the channel, as discussed below with respect to "pellets" of growth factor. The gel may be natural or synthetic, but the gel should be bio-compatible.

Carbodiimide chemistry may be used to conjugate a bioactive protein or other growth factors to the agarose gel. The agarose gel may be carboxylated in a reaction with mercaptoacetic acid. Then, the bioactive protein chains may be attached into the carboxylated-agarose using a carbodiimide kit by forming an amide bond between the agarose and the protein. Additional details about this procedure are available in N. Rahman, et al., "The use of vascular endothelial growth factor functionalized agarose to guide pluripotent stem cell aggregates toward blood progenitor cells," *Biomaterials*, vol. 31, pp. 8262-70, Nov, 2010, the entire contents of which are hereby incorporated by reference herein.

Figure 10:
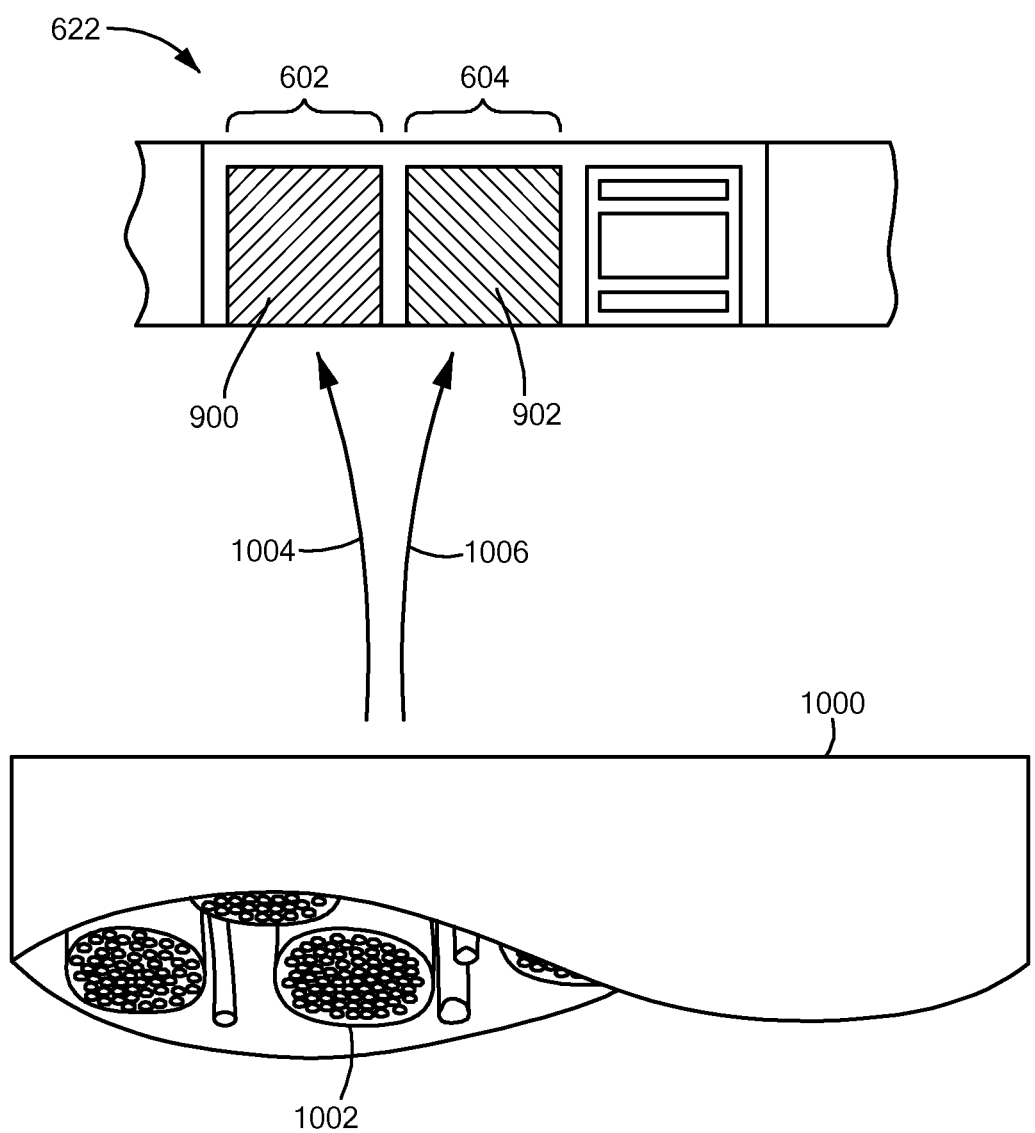
FIG. 10 is a top schematic view of a severed nerve and a scaffold of FIG. 9, with a top substrate of the scaffold removed for clarity, illustrating selective regeneration of axons of the nerve toward channels of the scaffold.

FIG. 10 is a top schematic view of a severed nerve 1000 and the scaffold 622 of FIG. 9 (with the top substrate 610 removed for clarity). Axons of a fascicle 1002 are selectively promoted to grow toward ones of the channels 602 and 604, as indicated by arrows 1004 and 1006, depending on the first and second growth factors included in the materials 900 and 902, respectively.

Although distribution of the growth factors within the first and second materials 900 and 902 may be uniform, a gradient in the distribution of the growth factors is believed to promote better selectivity, that is, better differentiation in which axon, or which type of axon, regenerates toward one of the channels 602, versus toward the other channel 604, and which axon, or which type of axon, regenerates toward channel 604, versus channel 602.

Figure 11:
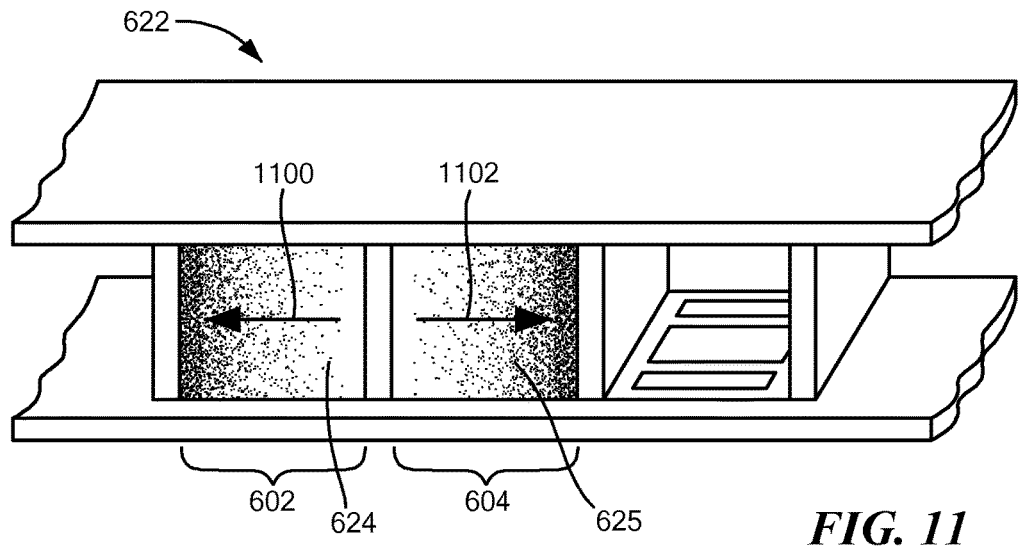
FIG. 11 is a perspective schematic diagram.
Figure 12:
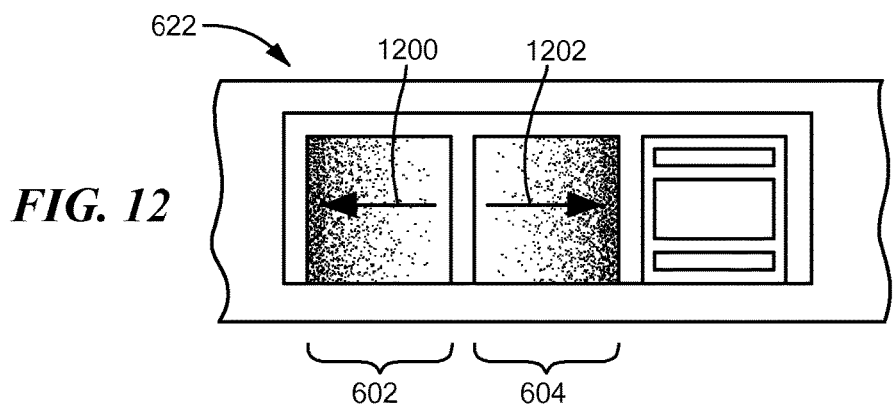
FIG. 12 is a schematic top view (with the top substrate removed for clarity), of the scaffold of FIG. 9, in which each of two adjacent channels contains a respective growth factor whose effectiveness varies across an opening of the channel in the scaffold, thereby forming a gradient of effectiveness of the growth factor, according to an embodiment of the present invention.

FIG. 11 is a perspective schematic diagram, and FIG. 12 is a schematic top view (with the top substrate 610 removed for clarity), of an embodiment in which each of two adjacent channels 602 and 604 contains a respective growth factor whose effectiveness varies across the openings 624 and 625 of the channels 602 and 604, thereby forming a gradient of effectiveness of the growth factor, with respect to its target axon or target axon type. The effectiveness of each growth factor is indicated by shading, where light shading indicates less effectiveness than dark shading. In addition, the effectiveness gradient is indicated by arrows 1100 and 1102, and arrows 1200 and 1202, pointing in directions of increasing effectiveness. The effectiveness of the two growth factors should increase in opposite directions, as indicated by the arrows 1100 and 1102, at least at the openings 624 and 625 of the channels 602 and 602.

Figure 13:
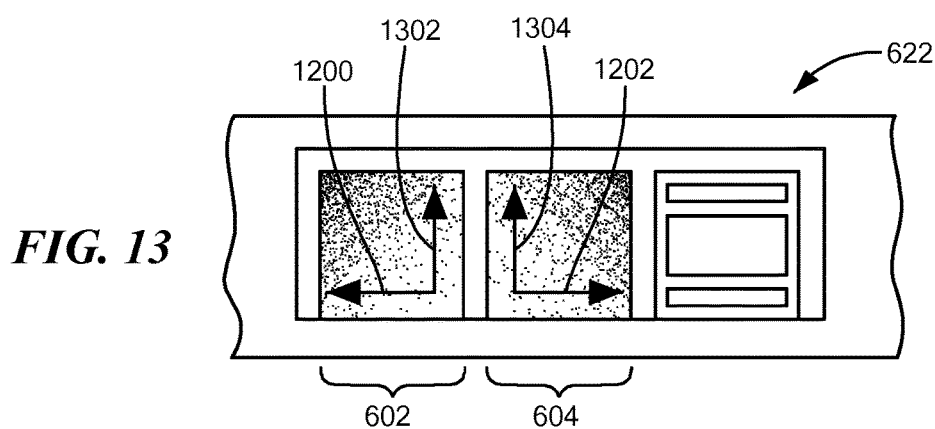
FIG. 13 is a top schematic view (with the top substrate removed for clarity) of the scaffold of FIG. 9, including a distribution of growth factors in two channels of the scaffold, such that the gradient increases along two dimensions, namely across the opening and along the length of each channel, according to an embodiment of the present invention.

In an alternative embodiment, schematically illustrated in FIG. 13 (a top view with the top substrate 610 removed for clarity), the gradient increases along two dimensions, namely across the opening (as indicated by arrows 1200 and 1202, as in the embodiment of FIGS. 11 and 12), but also along the length of each channel 602 and 604, increasing from front to back of each channel 602 and 604 as indicated by arrows 1302 and 1304.

The effectiveness gradients discussed above may be implemented in any suitable way. In some embodiments, concentration of the growth factor within the gel varies across the width of the channel 602 or 604. This variation in concentration may be continuous, as suggested by the gradual change in shading in FIGS. 11-13. Alternatively, the concentration may vary in discrete steps. (Not shown.)

Figure 14:
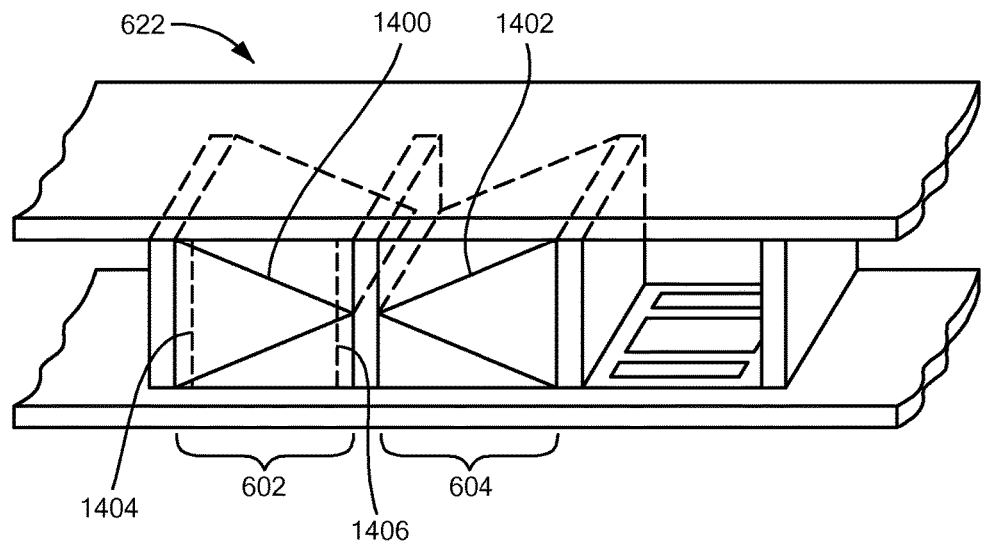
FIG. 14 is a front perspective schematic view of the scaffold of FIG. 9, including distribution of growth factors in two channels of the scaffold, according to another embodiment of the present invention.
Figure 15:
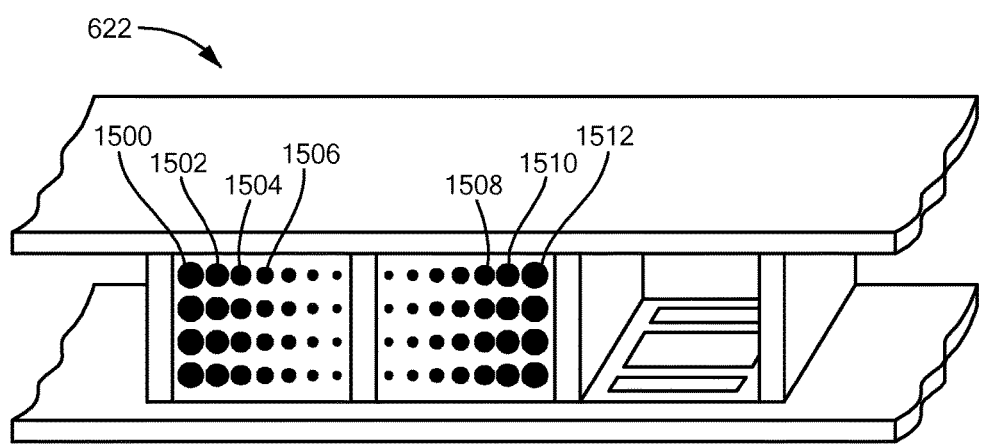
FIG. 15 is a front perspective schematic view.
Figure 16:
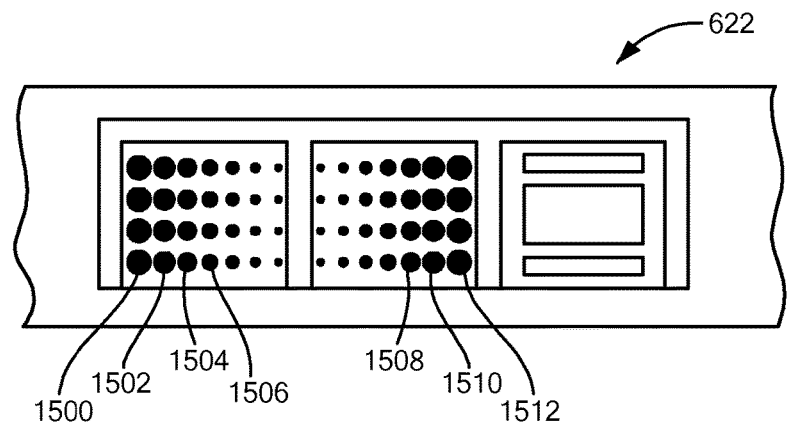
FIG. 16 is a top schematic view (with the top substrate removed for clarity), of the scaffold of FIG. 9, including distribution of growth factors in two channels of the scaffold, according to yet another embodiment of the present invention.

Alternatively, the effectiveness gradient may be implemented by varying an amount of growth factor disposed within the channel across its width, as schematically illustrated in FIG. 14. Here, the shaded portions 1400 and 1402 of the volumes of the channels 602 and 604, i.e., the triangular prism volumes, contain growth factor, and the unshaded portions do not. In the embodiment shown in FIG. 14, the amount of growth factor varies continuously, across the width of each channel 602 and 604. For example, a vertical stipe 1404 proximate the left side of the opening to channel 602 encounters more growth factor than a vertical stipe 1406 proximate the right side of the opening. However, as schematically illustrated in FIGS. 15 and 16, the growth factors may be disposed within the volumes of the channels 602 and 604 as discrete "pellets" whose volumes are indicated by relative sizes of dots 1500, 1502, 1504, 1506, 1508, 1510 and 1512. Optionally or alternatively, the amount of growth factor may vary from front to back of each channel 602 and 604 (not shown), along the lines discussed above, with respect to FIG. 13.

As noted, the volumes of the pellets of growth factor in FIGS. 15 and 16 vary in size across the width of each channel 602 and 604. Alternatively, as schematically illustrated in FIG. 17, all the pellets 1700, 1702, 1704, 1706 and 1708 may contain similar or identical amounts of growth factor, but the population density of pellets may vary across the width of each channel 602 and 604, thereby varying the effectiveness of the growth factor across the width of the channel.

Figure 17:
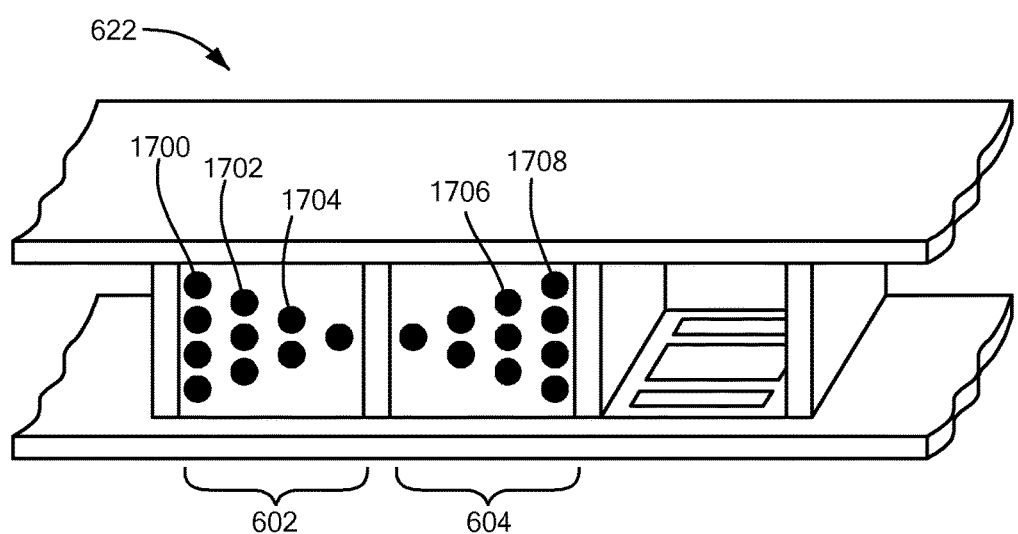
FIG. 17 is a front perspective schematic view.
Figure 18:
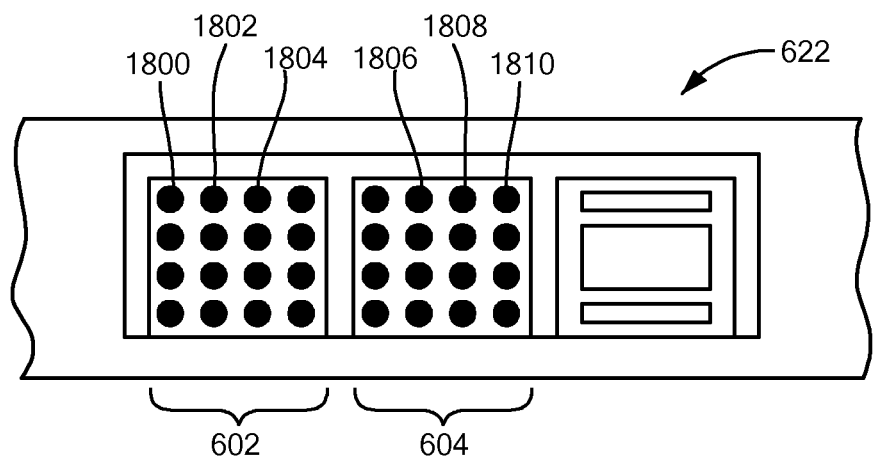
FIG. 18 is a top schematic view (with the top substrate removed for clarity), of the scaffold of FIG. 9, including distribution of growth factors in two channels of the scaffold, according to another embodiment of the present invention.
Figure 19:
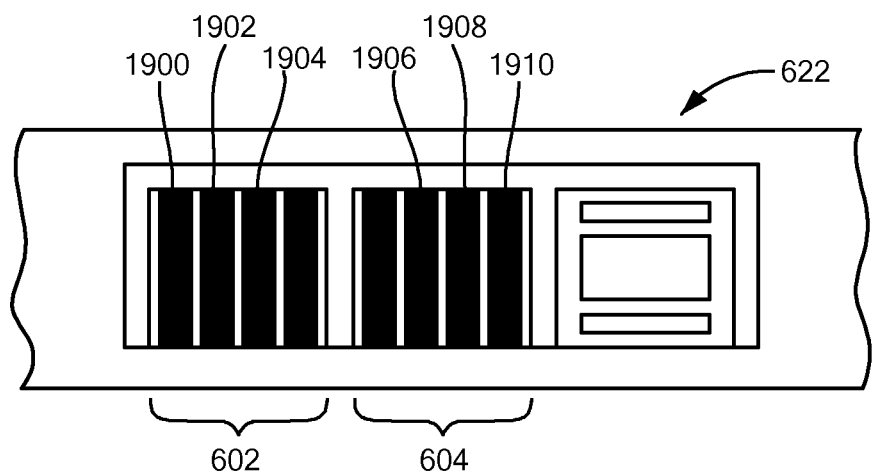
FIG. 19 is a top schematic view (with the top substrate removed for clarity) of the scaffold of FIG. 17, according to an alternative embodiment of the present invention.

FIGS. 18 and 19 schematically illustrate top views (with the top substrate 610 removed for clarity) of two versions of the embodiment of FIG. 17. In FIG. 18, each pellet 1800, 1802, 1804, 1806, 1808 and 1810 is approximately spherical, whereas in FIG. 19, each pellet 1900, 1902, 1904, 1906, 1908 and 1910 is approximately cylindrical (and oriented front-to-back within its respective channel 602 or 604). Other shapes of pellets may be used.

Figure 20:
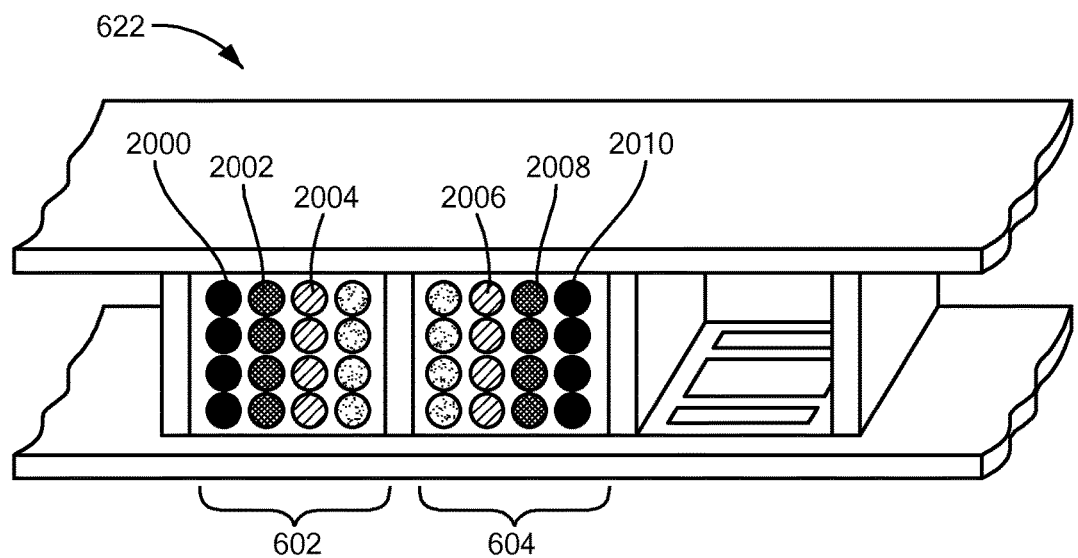
FIG. 20 is a front perspective schematic view.
Figure 21:
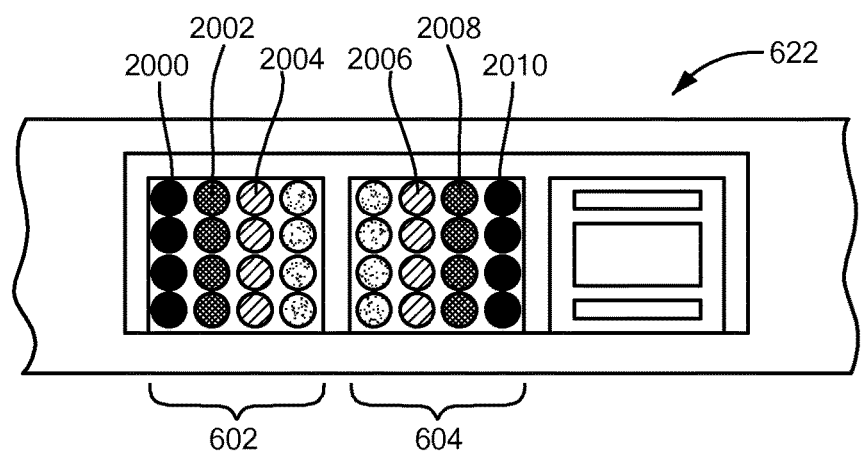
FIG. 21 is a top schematic view (with the top substrate removed for clarity), of the scaffold of FIG. 9, including distribution of growth factors in two channels of the scaffold, according to yet another embodiment of the present invention.

FIGS. 20 and 21 are respective schematic perspective and top views of another embodiment in which discrete pellets of growth factor are distributed in the volumes of the channels 602 and 604. However, in this embodiment, the concentrations in the pellets 2000, 2002, 2004, 2006, 2008 and 2010 vary, as indicated by fill pattern, with the fill pattern of pellet 2000 indicating a highest concentration, the fill pattern of pellet 2002 indicating a concentration less than that of pellet 2000 and the fill pattern of pellet 2004 indicating a concentration less than that of pellet 2002.

FIGS. 20 and 21 may also be used to schematically illustrate yet another embodiment, in which different growth factors, or different combinations of growth factors, may be used for different sets of pellets. For example, in one such embodiment, a first growth factor that is more effective than a second growth factor at promoting growth of efferent axons is included in pellet 2000, and the second growth factor is included in pellet 2002. A third growth factor, less effective than the second growth factor, is used in pellet 2004, and so forth. Another set of growth factors, which promote growth of afferent axons, may be used for pellets 2006, 2008 and 2010. Optionally, one or more growth factors or other substances that deter growth of efferent axons may be included, such as in progressively larger concentrations or amounts, in one or more of pellets 2000-2004, and one or more growth factors or other substances that deter growth of afferent axons may be included in one or more of pellets 2006-2010.

Gels that contain growth factors distributed so as to present gradients of effectiveness are referred to herein as anisotropic gels.

Figure 22:
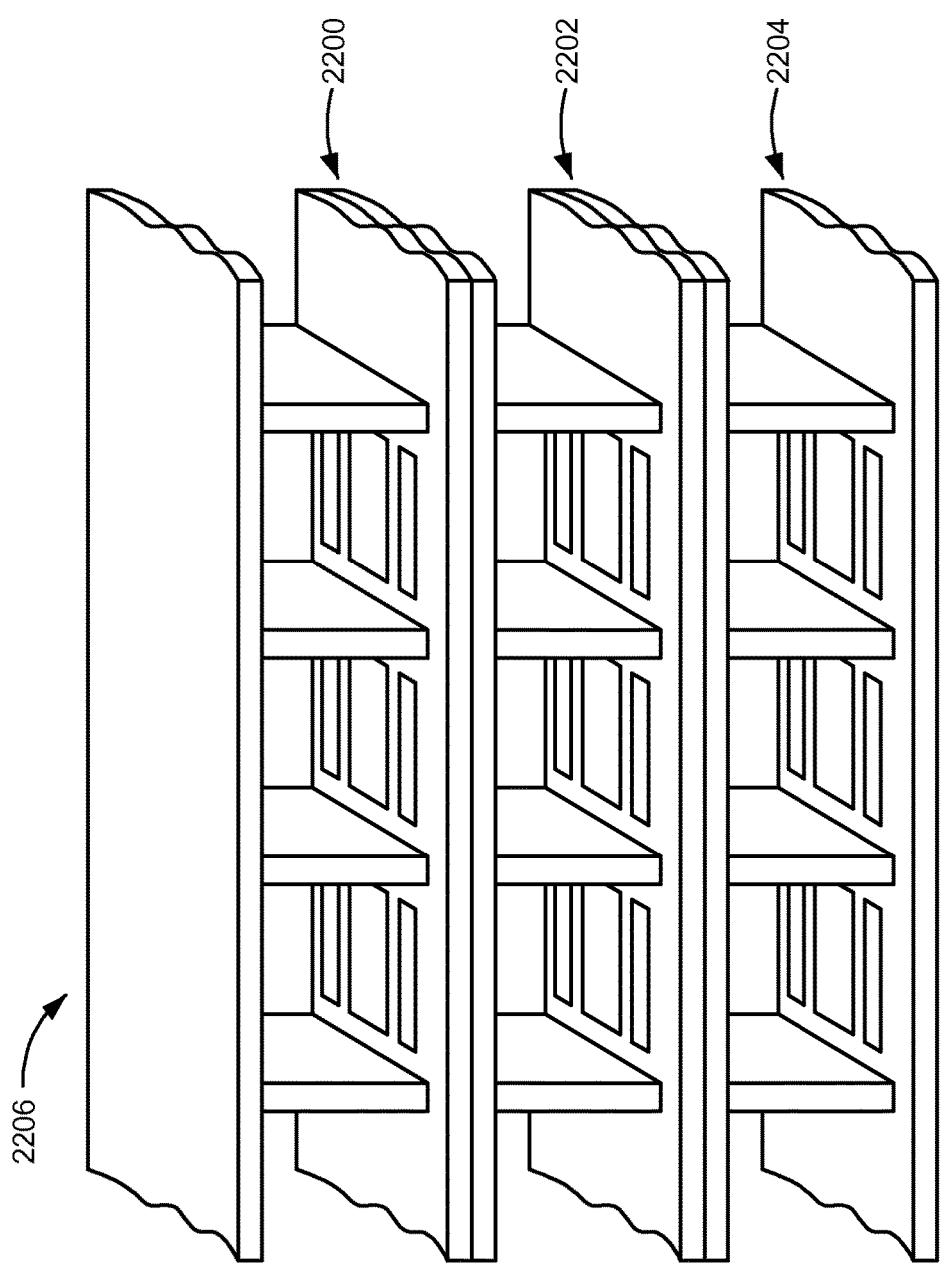
FIG. 22 illustrates several rows of scaffolds of FIG. 6 stacked together, according to an embodiment of the present invention.

Thus far, electrode arrays that include one row of channels have been described. However, as schematically illustrated in FIG. 22, two or more rows 2200, 2202 and 2204 of such electrode arrays may be stacked to form a two-dimensional array 2206 of channels. Each row's bottom substrate may form the top substrate of the row immediately below, or each row may include its own top and bottom substrate, and the rows may be joined by any suitable means. Plural rows of electrode arrays may be used, for example, when more channels are required within a desired horizontal dimension than can be included in a single row of electrodes.

Figure 23:
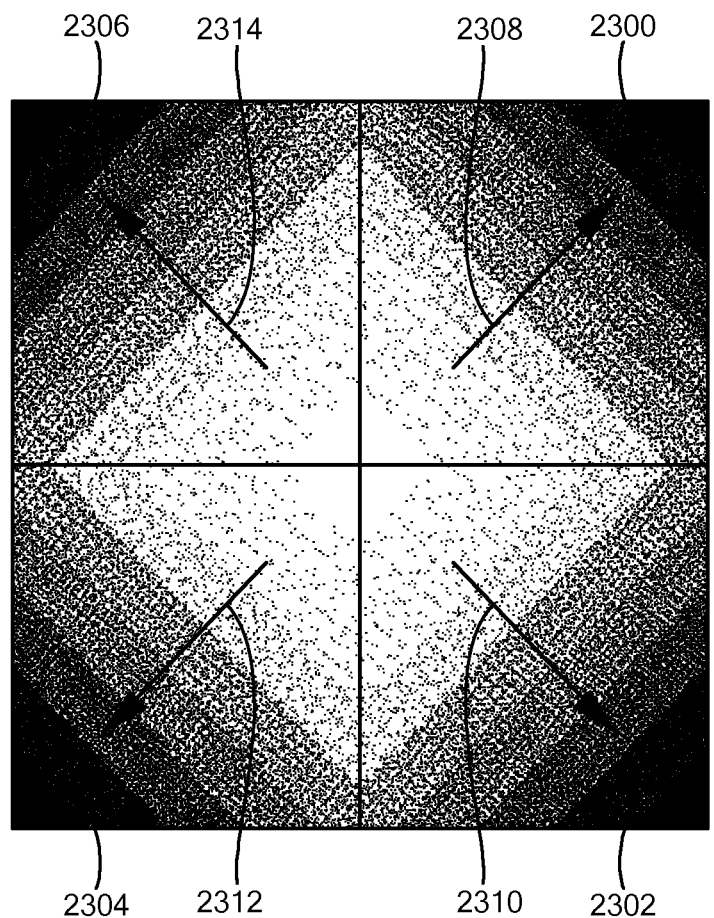
FIG. 23 schematically illustrates four openings to four respective channels of the stacked scaffold of FIG. 22, in which each of four adjacent channels contains a respective growth factor whose effectiveness varies across an opening of the channel in the scaffold, thereby forming a gradient of effectiveness of the growth factor, according to an embodiment of the present invention.

In another example, more than two different kinds of growth factors (each promoting growth of a respective type of nerve fiber) may be used to selectively promote growth of more than two kinds of nerve fiber. For example, FIG. 23 schematically illustrates four openings 2300, 2302, 2304 and 2306 to four respective channels. Each of the channels contains a growth factor whose gradient is schematically illustrated by a respective arrow 2308, 2310, 2312 and 2314.

As can be seen in FIG. 23, the gradients increase along respective directions radially away from a point 2316 surrounded by the respective openings 2300-2306, although the point 2316 need not necessarily be located at the intersection of all four of the openings 2300-2306. All the growth factors in the four channels need not be different from each other. That is, two or more of the channels may contain similar or identical growth factors.

Figure 24:
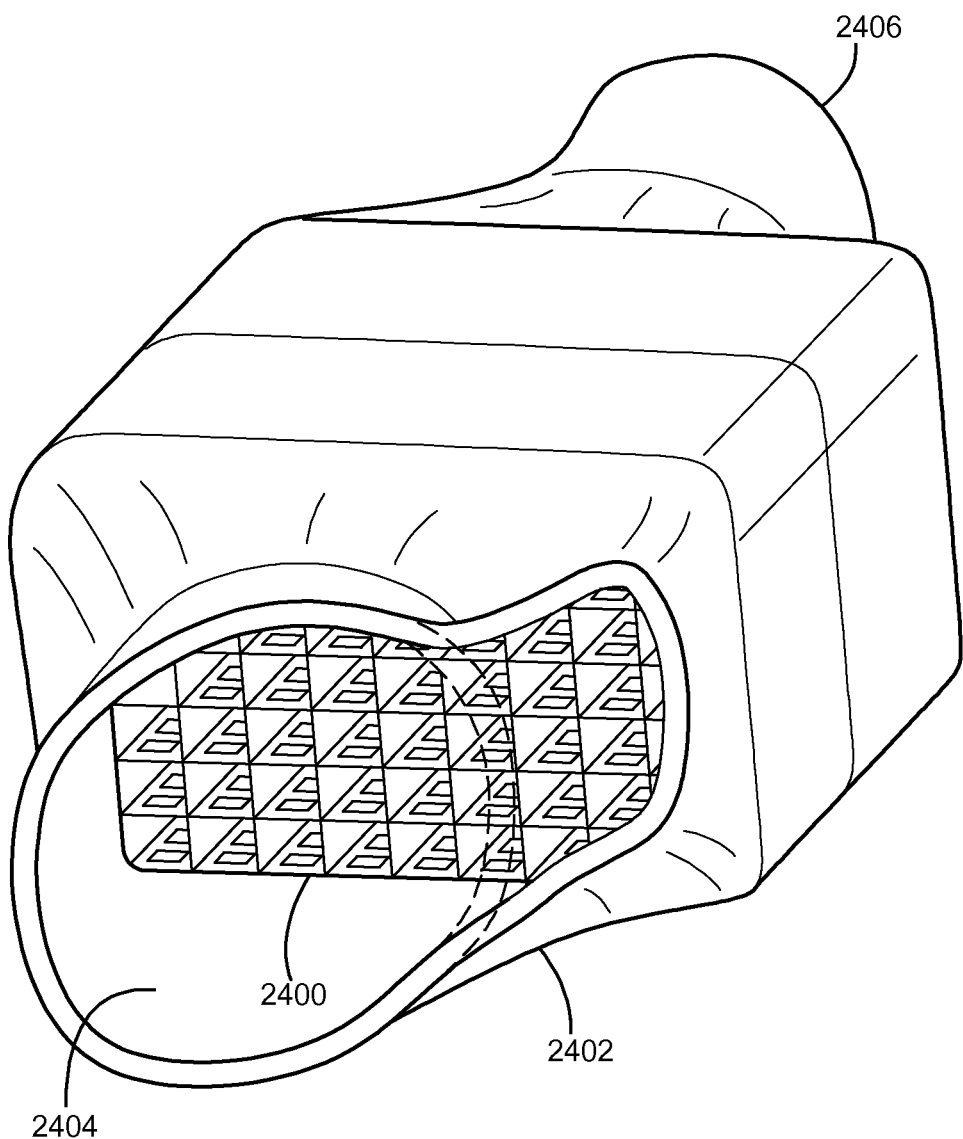
FIG. 24 is a partially cut-away perspective illustration of the stacked scaffold of FIG. 22 in a housing, according to an embodiment of the present invention.

Optionally, as illustrated in FIG. 24, an electrode array 2400 may be enclosed in a flexible housing 2402 having a first opening 2404, through which a severed nerve may be inserted, and a second opening 2406, through which wires connected to the respective electrodes may emerge. The housing 2402 should be made of a bio-compatible material. A heat-shrinkable material may facilitate attaching the housing 2402 to the electrode array 2400.

Figure 25:
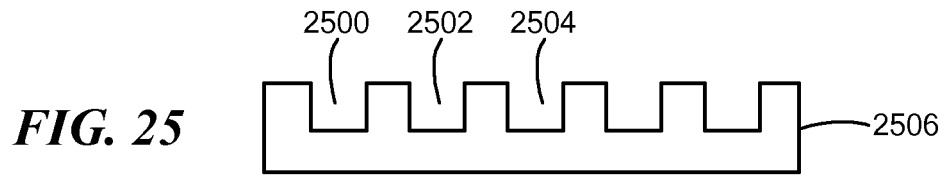
FIGS. 25-34 schematically illustrate stages of fabrication of the stacked scaffold of FIG. 22, according to an embodiment of the present invention.

FIGS. 25-34 schematically illustrate stages of fabrication of a two-dimensional electrode array, such as the array 2206 of FIG. 22. FIG. 25 shows channels, exemplified by channels 2500, 2502 and 2504, formed in a PDMS substrate 2506. The channels may be formed by any suitable method. Methods of forming channels in PDMS are well known, as exemplified by T. Kniazeva, et al., "A microfluidic respiratory assist device with high gas permeance for artificial lung applications," *Biomed Microdevices*, vol. 13, pp. 315-23, Apr. 2011 (hereinafter "Kniazeva"), the contents of which are hereby incorporated by reference herein as needed for explaining channel formation in PDMS.

Figure 26:
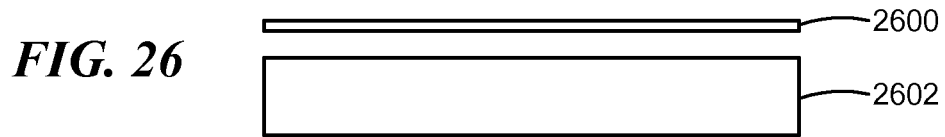
Figure 27:
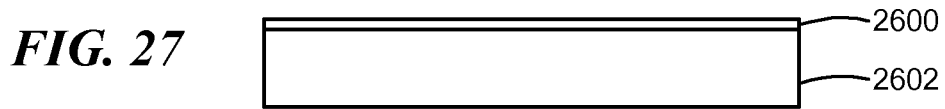
Figure 28:
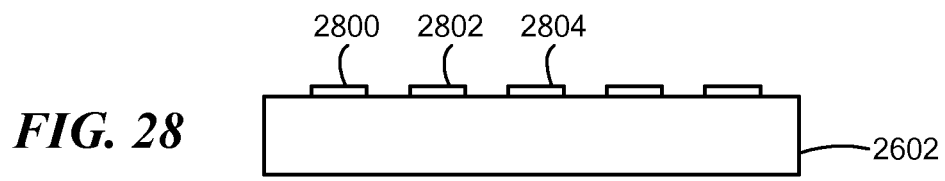

FIGS. 26 and 27 illustrate spinning a platinum foil 2600 onto a PDMS substrate 2602 to laminate the platinum foil onto the PDMS substrate. In FIG. 28, the platinum foil 2600 is patterned, such as by a laser, to leave electrodes, exemplified by electrodes 2800, 2802 and 2804, meandering traces (not visible) and interconnect pads (not visible) to facilitate later attaching wires.

Figure 29:
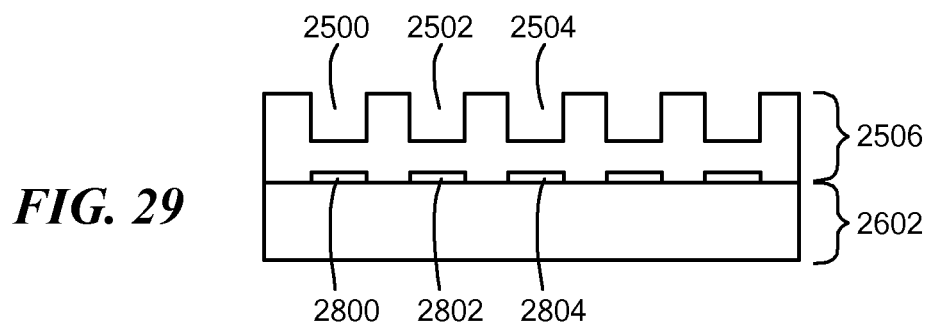
Figure 30:
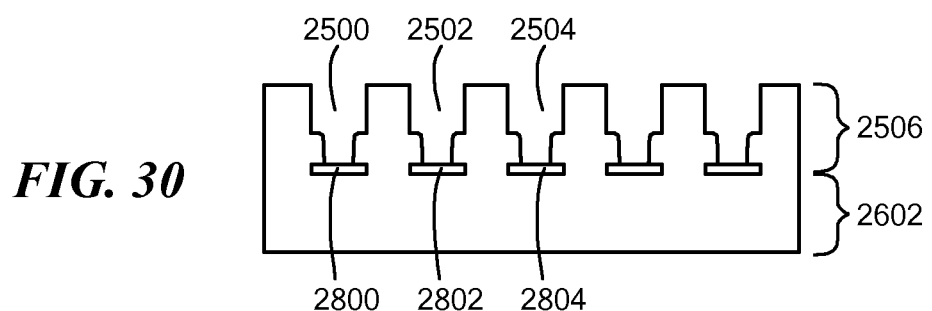
Figure 31:
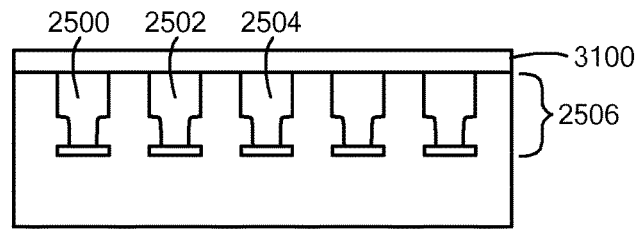
Figure 32:
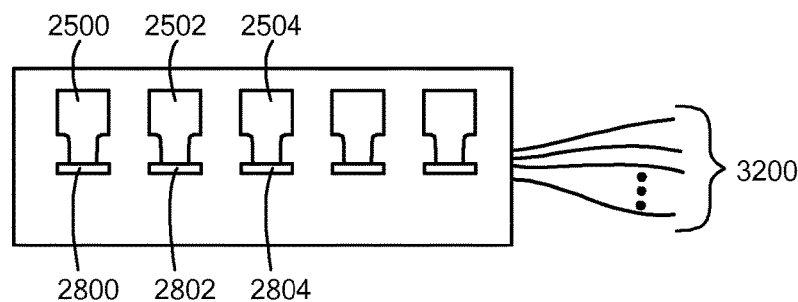

FIG. 29 illustrates the channeled PDMS substrate 2506 having been bonded, such as via oxygen-plasma bonding, to the electrode substrate 2602. FIG. 30 shows the PDMS substrate 2506 after holes are drilled, such as by a laser, in each channel 2500-2504 to expose the channel's corresponding electrode 2800-2804. FIG. 31 illustrates a PDMS lid 3100 being laminated to the PDMS substrate 2506. In some embodiments, the lid 3100 is about 50μ thick. In FIG. 23, wires 3200 are electrically connected, such as by welding, to interconnect pads (not visible) that were formed at the stage represented by FIG. 28. Growth factors (chemotropic agents) may be introduced into the channels 2500-2502 at this time.

Figure 33:
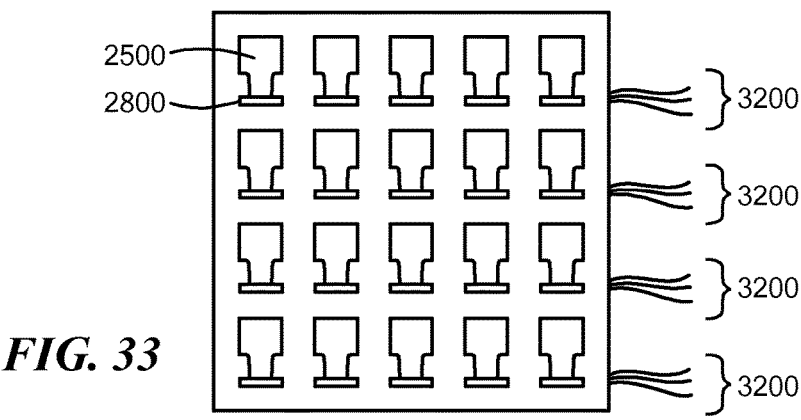
Figure 34:
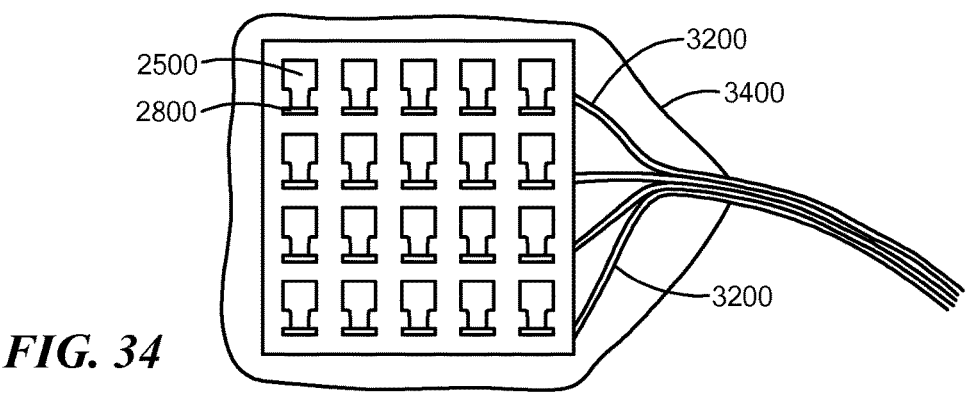

FIG. 33 illustrates several rows of channels stacked. The channels may be stacked by any suitable method. Methods of stacking PDMS channels are well known, as exemplified by Kniazeva, the contents of which are hereby incorporated by reference herein as needed for explaining PDMS channel stacking. A back wall substrate may be bonded to the stacked channels, or each row of channels may have a back wall substrate bonded to it, as it is fabricated (not shown). FIG. 34 shows the stack of channel rows and wires 3200 overmolded with a biocompatible substance, such as silicone 3400.

Figure 35:
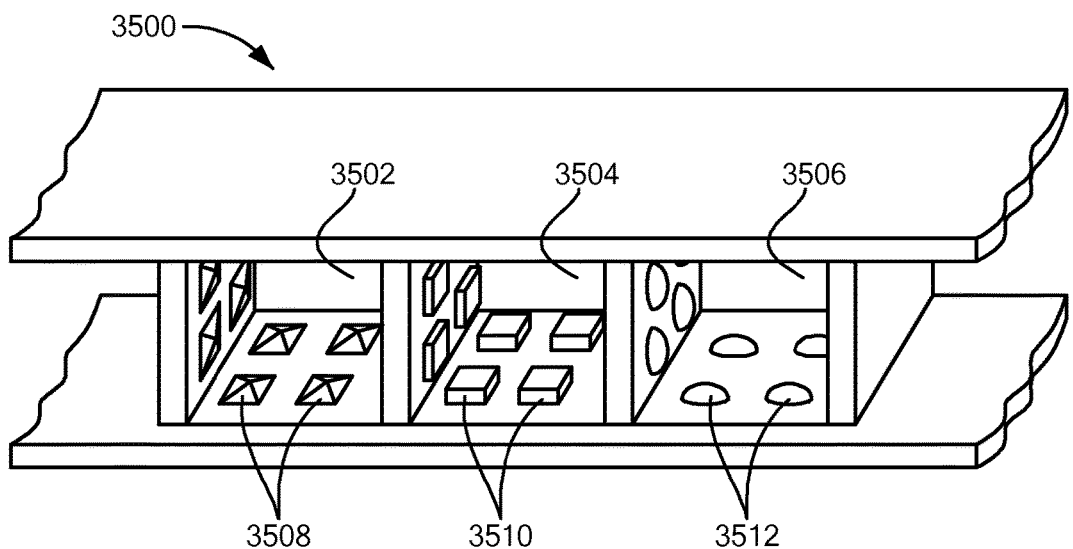
FIG. 35 is a perspective schematic view of a portion of an electrode array, according to another embodiment of the present invention.

Although growth factors have been described as being disposed within channels of electrode arrays to selectively promote growth of nerve fibers, in some embodiments, three-dimensional surface patterns on interior walls of the channels may be used to selectively promote growth of the nerve fibers. FIG. 35 is a perspective view of a portion of an electrode array 3500 that includes a different three-dimensional pattern in each of three channels 3502, 3504 and 3506. The floor, walls and ceiling of channel 3502 include pyramid-shaped projections extending into the channel 3502. Channel 3504 includes rectangular projections, and channel 3506 includes round projections. Although a 2×2 array of projections is shown on each surface of the channels 3502-3506, other numbers of projections may be used, other shapes and combinations of shapes may be used and the projections may be present on any number of the surfaces of the channels. In some embodiments, wall of some channels may include patterns, while walls of other channels may be smooth. Surface patterns may be used alone or in combination with growth factors in a given embodiment.

Thus, embodiments of the present invention may be used to interface with peripheral nerves to restore motor action in the periphery and/or provide neural feedback from artificial sensors. Although uses of embodiments of the present invention have been described in the context of limb amputation, these and other embodiments may be used for restoring motor, sensory and/or other functions in patients with spinal cord injuries, brain injuries, neurodegenerative diseases or other diseases or injuries or issues.

Various dimensions and numbers of rows and columns of channels may be used, depending on an intended use of the scaffold. Exemplary nerves that may be terminated in, or regenerated through, embodiments of the present invention and their corresponding applications are listed in Table 1.

TABLE 1

Exemplary Applications

| Nerve | Application |
|---|---|
| Hypoglossal nerve | Tongue control for obstructive sleep apnea |
| Vagus nerve | Depression, epilepsy and other |
| Cauda equina (spinal root) | Bladder control |
| Sciatic nerve | Motor control |
| Phrenic nerve | Sleep apnea and lung control |
| Pudental nerve | Interstitial cystitis |
| Spinal nerves | Asthma and pain |

Another embodiment of the present invention (not shown) that defines both a front opening and a back opening to each channel facilitates rejoining a severed nerve by placing one of the two severed nerve ends proximate the front openings and placing the other of the two severed nerve ends proximate the back openings the back openings. Electrophysiological activity of the regenerating nerve may then be monitored, as the nerve rejoins within the scaffold. Thus, this embodiment may be used as a diagnostic tool.

The presence of electrodes and bioactive matrix that navigates specific axons into specific channels enables functional stimulation of specific axons. Hence, the device may also be used as a therapeutic device.

On-chip electronics may be included in a scaffold, between the electrodes and the wire leads, to multiplex signals from or to several of the electrodes to or from a single wire, thereby reducing interconnect burden.

While the invention is described through the above-described exemplary embodiments, modifications to, and variations of, the illustrated embodiments may be made without departing from the inventive concepts disclosed herein. Furthermore, disclosed aspects, or portions thereof, may be combined in ways not listed above and/or not explicitly claimed. Accordingly, the invention should not be viewed as being limited to the disclosed embodiments.

What is claimed is:

1. An electrode array, comprising:
   (1) a bio-compatible dielectric scaffold defining a plurality of openings and a plurality of channels therein, wherein each channel:
      (a) occupies a three-dimensional volume extending into the scaffold from a respective opening of the plurality of openings;
      (b) contains an electrode attached to the scaffold and electrically exposed to the three-dimensional volume of the channel; and
      (c) contains a bio-compatible gel disposed therein;
   (2) a first growth factor disposed in the gel disposed in a first at least one of the plurality of channels, wherein the first growth factor is selected to preferentially promote growth of a first type of nerve fiber over a second type of nerve fiber; and
   (3) a second growth factor disposed in the gel disposed in a second at least one of the plurality of channels, different than the first at least one of the plurality of channels, wherein the second growth factor is selected to preferentially promote growth of the second type of nerve fiber over the first type of nerve fiber; wherein:
   the first growth factor is disposed in the gel disposed in the first at least one of the plurality of channels so as to present a first gradient of effectiveness of the first growth factor across the opening of the first at least one of the plurality of channels;
   the second growth factor is disposed in the gel disposed in the second at least one of the plurality of channels so as to present a second gradient of effectiveness of the second growth factor across the opening of the second at least one of the plurality of channels;
   the first gradient increases along a direction away from the opening of the second at least one of the plurality of channels; and
   the second gradient increases along a direction away from the opening of the first at least one of the plurality of channels.

2. An electrode array according to claim 1, wherein:
   the first type of nerve fiber comprises afferent nerve fiber; and
   the second type of nerve fiber comprises efferent nerve fiber.

3. An electrode array according to claim 1, wherein:
   the first type of nerve fiber comprises a first type of efferent nerve fiber; and
   the second type of nerve fiber comprises a second type of efferent nerve fiber, different than the first type of efferent nerve fiber.

4. An electrode array according to claim 3, wherein:
   the first type of nerve fiber comprises skin efferent nerve fiber; and
   the second type of nerve fiber comprises muscle efferent nerve fiber.

5. An electrode array according to claim 1, wherein:
   the first growth factor comprises at least one of: a close homolog of L1 (CHL1), L1-CAM and neurocan; and
   the second growth factor comprises at least one of: netrin-1, semaphorin III and neuropilin-1.

6. An electrode array according to claim 1, wherein:
   the plurality of channels is arranged in a two-dimensional array; and further comprising:
   a third growth factor disposed in the gel disposed in a third at least one of the plurality of channels so as to present a third gradient of effectiveness of the third growth factor across the opening of the third at least one of the plurality of channels; and
   a fourth growth factor disposed in the gel disposed in a fourth at least one of the plurality of channels so as to present a fourth gradient of effectiveness of the fourth growth factor across the opening of the fourth at least one of the plurality of channels; wherein:
   the respective openings of the first, second, third and fourth at least one of the plurality of channels are arranged in a 2×2 array;
   the third gradient increases along a direction away from the opening of the first at least one of the plurality of channels; and
   the fourth gradient increases along a direction away from the opening of the second at least one of the plurality of channels.

7. An electrode array according to claim 6, wherein the first, second, third and fourth gradients increase along respective directions radially away from a point surrounded by the respective openings of the first, second, third and fourth at least one of the plurality of channels.

8. An electrode array according to claim 1, wherein the plurality of channels is arranged in a two-dimensional array.

9. An electrode array according to claim 1, wherein each opening has a major diameter no greater than about 200 µm.

10. An electrode array according to claim 1 wherein, for each channel of the plurality of channels, the scaffold defines a back wall that defines an extent to which the three-dimensional volume of the channel extends into the scaffold.

11. An electrode array according to claim 1 wherein, for each channel of the plurality of channels, the growth factor disposed in the gel disposed in the channel is conjugated to the gel.

12. An electrode array, comprising:
   a bio-compatible dielectric scaffold defining a plurality of openings and a plurality of channels therein, wherein each channel:
      (a) occupies a three-dimensional volume extending into the scaffold from a respective opening of the plurality of openings;
      (b) contains an electrode attached to the scaffold and electrically exposed to the three-dimensional volume of the channel; and
      (c) is defined at least in part by at least one wall of the scaffold, wherein the at least one wall defines a three-dimensional surface pattern; wherein:
   the surface pattern of a first channel of the plurality of channels is different than the surface pattern of a second channel of the plurality of channels.

13. An electrode array according to claim 12, further comprising:
   for each channel of the plurality of channels, a bio-compatible gel disposed therein;
   a first growth factor disposed in the gel disposed in a first at least one of the plurality of channels, wherein the first growth factor is selected to preferentially promote growth of a first type of nerve fiber over a second type of nerve fiber; and
   a second growth factor disposed in the gel disposed in a second at least one of the plurality of channels, different than the first at least one of the plurality of channels, wherein the second growth factor is selected to preferentially promote growth of the second type of nerve fiber over the first type of nerve fiber.

14. An electrode array according to claim 12, wherein the surface pattern of the first channel of the plurality of channels comprises rectangular bumps.

15. An electrode array according to claim 12, wherein the surface pattern of the first channel of the plurality of channels comprises pyramidal bumps.

16. An electrode array according to claim 12, wherein the surface pattern of the first channel of the plurality of channels comprises round bumps.

* * * * *